United States Patent
Suzuki et al.

(10) Patent No.: US 7,452,332 B2
(45) Date of Patent: Nov. 18, 2008

(54) REPORT ON CHANGES OVER TIME IN BLOOD VESSEL ELASTICITY INDEXES AND BIOINFORMATION OUTPUT APPARATUS

(75) Inventors: Tsuneo Suzuki, Saitama-ken (JP); Norio Sato, Chiba-ken (JP)

(73) Assignee: Fukuda Denshi Co., Ltd., Tokyo (JP)

(*) Notice: Subject to any disclaimer, the term of this patent is extended or adjusted under 35 U.S.C. 154(b) by 0 days.

(21) Appl. No.: 11/453,848

(22) Filed: Jun. 16, 2006

(65) Prior Publication Data
US 2007/0004985 A1    Jan. 4, 2007

(30) Foreign Application Priority Data
Jun. 17, 2005    (JP)    ............. 2005-178312

(51) Int. Cl.
*A61B 5/02*    (2006.01)
*A61B 5/04*    (2006.01)

(52) U.S. Cl. .................. 600/483; 600/485; 600/481

(58) Field of Classification Search ......... 600/481–486, 600/488, 490–507
See application file for complete search history.

(56) References Cited

U.S. PATENT DOCUMENTS

| 6,669,646 | B1 |  | 12/2003 | Narimatsu et al. |
| 7,029,449 | B2 | * | 4/2006 | Ogura ............... 600/500 |
| 2005/0256412 | A1 | * | 11/2005 | Shimazu et al. ........ 600/500 |
| 2006/0173366 | A1 | * | 8/2006 | Hasegawa ............ 600/485 |

FOREIGN PATENT DOCUMENTS

| EP | 1 050 267 A1 | 11/2000 |
| EP | 1 203 558 A2 | 5/2002 |
| EP | 1 332 716 A1 | 8/2003 |
| EP | 1 348 373 A1 | 10/2003 |
| EP | 1348373 A1 | 10/2003 |
| JP | 2000-316821 | 11/2000 |
| JP | 2005-152449 | 6/2005 |
| RU | 94025550 A1 | 5/1996 |
| WO | 02/31642 A1 | 4/2002 |

OTHER PUBLICATIONS

Russian Office Action issued May 28, 2007 in Russian Application No. 2006121384/(023218).
Woodman, R. J. et al., "Measurement and Application of Arterial Stiffness in Clinical Research: Focus on New Methodologies and Diabetes Mellitus", Watts: Med. Sci Monitor, (2003), vol. 9, No. 5, pp. 101-109 (i.

(Continued)

*Primary Examiner*—Charles A. Marmor, II
*Assistant Examiner*—Navin Natnithithadha
(74) *Attorney, Agent, or Firm*—Drinker Biddle & Reath LLP

(57) ABSTRACT

A report on changes over time is generated and outputted that presents, in addition to the changes of blood vessel elasticity indexes, the changes over time of other measured values of bioinformation related to vascular disease such as a blood pressure value in time series. This report is useful for a diagnosis with respect to vascular disease from various aspects.

10 Claims, 9 Drawing Sheets

OTHER PUBLICATIONS

Vilkov, V. G., "Early Detection of Arterial Hypertension by Functional Techniques", Moscow, (2002), p. 54 (including partial translation).

Bulletin of the Scientific Center for Cardiovascular Surgery (NTsSSKh) named after A. N. Bakulev, Cardiovascular Diseases, Addendum, (2006), No. 6; p. 39, Fig. 79; p. 70, Figs. 162-164 (including translation).

Russian Decision to Grant mailed Jan. 30, 3008 issued in Russian Application No. 2006121384/14(023218) (including a partial translation thereof).

* cited by examiner

FIG. 2

| 1 | $= \dfrac{1}{k^2} \times \left(\ln \dfrac{Ps}{Pd}\right) \times (PWV)^2$ | $= \sqrt{\dfrac{1}{k^2} \times \left(\ln \dfrac{Ps}{Pd}\right) \times (PWV)^2}$ |
|---|---|---|
| 2 | $= k \times \dfrac{\left(\ln \dfrac{Ps}{Pd}\right) \times (PWV)^2}{(Ps - Pd)}$ | $= \sqrt{k \times \dfrac{\left(\ln \dfrac{Ps}{Pd}\right) \times (PWV)^2}{(Ps - Pd)}}$ |
| 3 | $= k \times \dfrac{(PWV)^2}{Pd}$ | $= \sqrt{k \times \dfrac{(PWV)^2}{Pd}}$ |
| 4 | $= \dfrac{1}{k^2} \times \left(\ln \dfrac{Pm}{Pd}\right) \times (PWV)^2$ | $= \sqrt{\dfrac{1}{k^2} \times \left(\ln \dfrac{Pm}{Pd}\right) \times (PWV)^2}$ |
| 5 | $= k \times \dfrac{\left(\ln \dfrac{Pm}{Pd}\right) \times (PWV)^2}{(Pm - Pd)}$ | $= \sqrt{k \times \dfrac{\left(\ln \dfrac{Pm}{Pd}\right) \times (PWV)^2}{(Pm - Pd)}}$ |

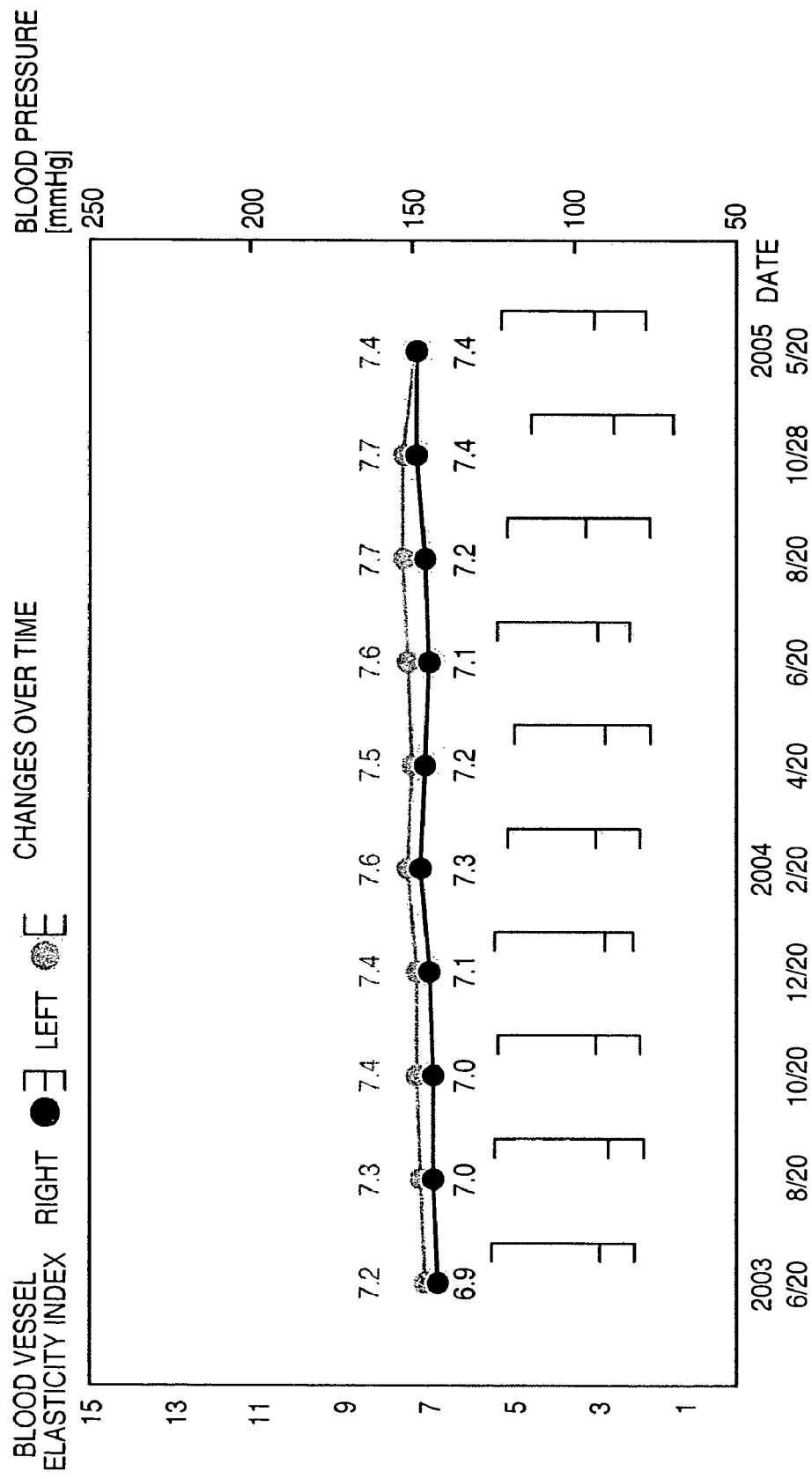

FIG. 4A
(SYSTOLIC) —
(MEAN) —
(DIASTOLIC) —
FIG. 4B
FIG. 4C
FIG. 4D
FIG. 4E
FIG. 4F
FIG. 4G
←
←
←
FIG. 4H
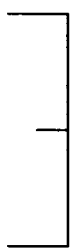
FIG. 4I
FIG. 4J
FIG. 4K

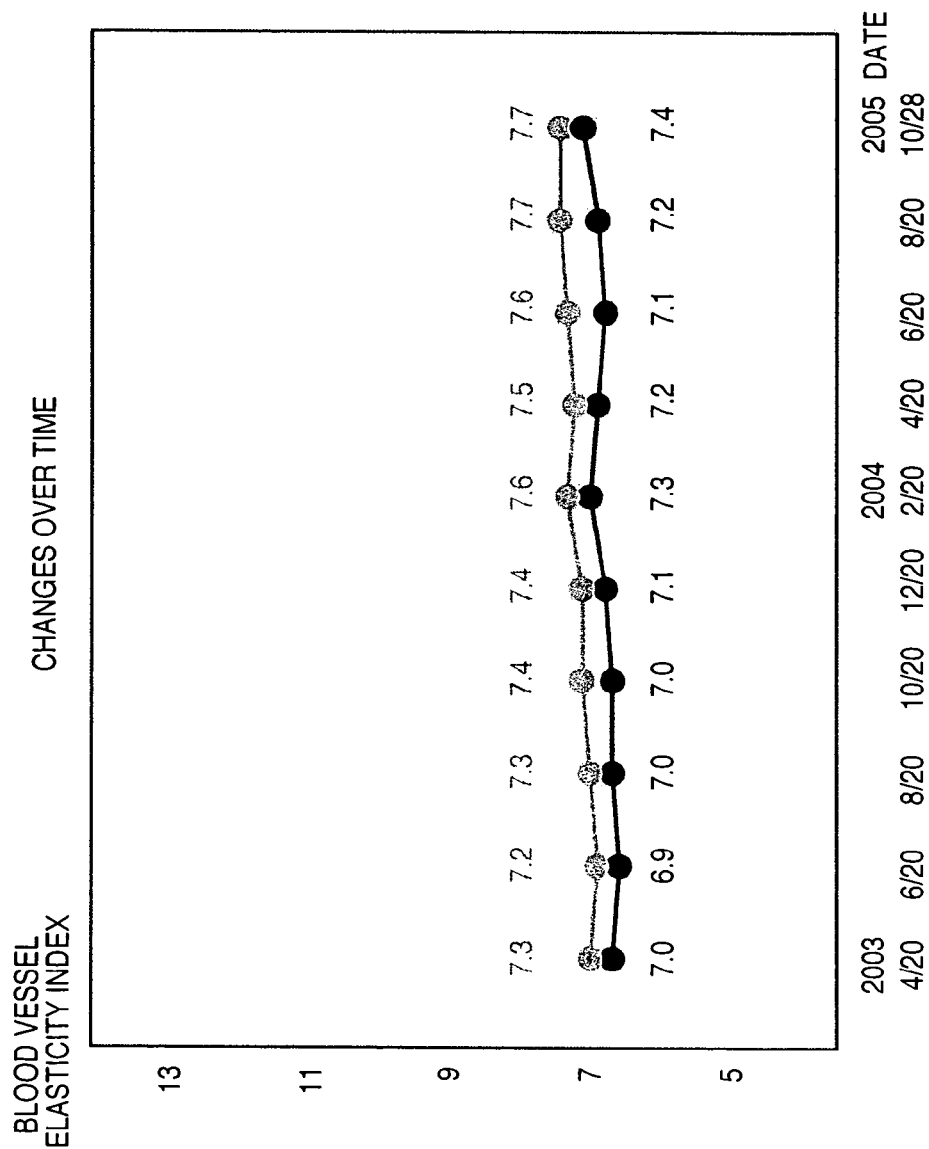

REPORT ON CHANGES OVER TIME IN BLOOD VESSEL ELASTICITY INDEXES AND BIOINFORMATION OUTPUT APPARATUS

CLAIM OF PRIORITY

This application claims priority from Japanese Patent Application No. 2005-178312, filed on Jun. 17, 2005, which is hereby incorporated by reference herein.

FIELD OF THE INVENTION

The present invention relates to a method to output bioinformation, in particular, an output report format to present a change over time in blood vessel elasticity indexes which functions as an indicator of arterial disease. The present invention also relates to a bioinformation output apparatus to output such a report.

BACKGROUND OF THE INVENTION

Conventionally, a ratio between blood pressures measured in a lower extremity and an upper extremity (a ratio between blood pressures in lower extremity and upper extremity) and a pulse wave propagate velocity or pulse wave velocity (Pulse Wave Velocity: PWV) are generally used as indicators of vascular disease such as arteriosclerosis (see, for example, Japanese Patent Laid-Open No. 2000-316821). For example, ABI, a ratio between systolic blood pressures measured in brachium and ankle, and TBI, a ratio between blood pressures measured in brachium and toe, are known as examples of a ratio between blood pressures in lower extremity and upper extremity, and ABI and TBI are used as indicators to show the presence or absence of arterial stenosis in lower extremity. On the other hand, a PWV is a propagation velocity of a wave generated with a movement of a vessel wall pressure in the aorta, the pressure being provided to a vessel wall when a heart feeds blood to the aorta. The faster velocity indicates a harder blood vessel. A PWV is calculated by measuring the same pulse wave at two different points on a blood vessel and a propagation time of the pulse wave, and dividing the distance between the two points by the propagation time.

However, since the pulse wave propagation velocity is affected by a blood pressure, correction is practically required depending on the blood pressure value. Moreover, because the relation between the blood pressure value and the amount of correction depends on the site in a body, the relation with respect to individual site should be examined beforehand, which virtually limits the sites to measure a pulse wave propagation time.

To solve the above problem, the applicant of the present invention has proposed the following formula as another indicator (see Japanese Patent Laid-Open No. 2005-152449):

Blood vessel elasticity index=$1/k^2(\ln(P_s/P_d)) \cdot PWV^2$ (where, $k^2$ is a constant, Ps is a systolic blood pressure, and Pd is a diastolic blood pressure)

The blood vessel elasticity index (sometimes referred to as a degree of a vascular sclerosis) is useful as an indicator presenting the state of blood vessel at the time of measurement. On the other hand, because the vascular disease such as arteriosclerosis is so-called adult disease, regular measurements and observation of changes over time in the measured results is also important.

FIG. 9 is a conventional format to show changes over time in blood vessel elasticity indexes. This format presents the values, which were measured before on a common patient, in a two dimensional graph with a horizontal axis representing date, and a vertical axis presenting blood vessel elasticity index. The blood vessel elasticity indexes on left side body and right side body are presented in a separate sequence respectively.

In FIG. 9, the presentation of a plurality of measured values over time allows the changes over time in each blood vessel elasticity index to be understood by glancing at it, and a tendency toward deterioration or amelioration of symptoms to be checked.

However, there are useful other information such as ABI and blood pressure, in addition to the blood vessel elasticity index, in bioinformation related to vascular disease. It can be thought that a diagnosis from various perspectives can be made if changes over time in such information are also taken into account together with the changes over time in blood vessel elasticity indexes. However, because conventionally only the changes over time in blood vessel elasticity indexes have been presented, such report was used only for a diagnosis from the perspective of blood vessel elasticity index.

SUMMARY OF THE INVENTION

The present invention is made in view of the above problems in prior art, and one object of the present invention is to provide a report on changes over time in blood vessel elasticity indexes which is useful for a diagnosis on vascular disease from various aspects, and a bioinformation output apparatus which is able to output such a report.

That is, a gist of the present invention lies in a report on changes over time in blood vessel elasticity indexes to present the changes over time in measured results of blood vessel elasticity indexes with respect to a common subject, comprising a graph area with a horizontal axis representing time and a vertical axis representing values of blood vessel elasticity indexes, wherein each of the blood vessel elasticity indexes is plotted in time series by positioning a first indicator at a coordinate which is defined by a measured date and a value in the graph area, and wherein a measured value of bioinformation relative to vascular disease other than the blood vessel elasticity index which is measured simultaneously with the blood vessel elasticity index is plotted in time series in the graph area in association with the corresponding blood vessel elasticity index.

Another gist of the present invention lies in a bioinformation output apparatus, comprising: obtaining means for obtaining from a storage device, measured values of at least a blood vessel elasticity index and other bioinformation related to one or more vascular diseases which are measured in a common subject; report generating means for generating a report on changes over time in the blood vessel elasticity indexes; and outputting means for outputting the generated report on the changes over time in blood vessel elasticity indexes, wherein the report generating means generates a report on changes over time in blood vessel elasticity indexes according to the present invention.

According to the above-described configuration, the present invention makes it possible to provide a report useful to a diagnosis on a vascular disease state from various aspects, by presenting the measured results over time on the other bioinformation related to vascular disease in the report on the changes over time in blood vessel elasticity indexes according to the common time scale.

Other objects and advantages besides those discussed above shall be apparent to those skilled in the art from the description of a preferred embodiment of the invention which follows. In the description, reference is made to accompanying drawings, which form a part thereof, and which illustrate an example of the various embodiments of the invention. Such example, however, is not exhaustive of the various embodiments of the invention, and therefore reference is made to the claims which follow the description for determining the scope of the invention.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 2 is a diagram to show examples of formulae to calculate a blood vessel elasticity index, which is necessary for a bioinformation output apparatus according to an embodiment.

FIG. 3 is a diagram to explain a format of a report on changes over time, which is output with a bioinformation output apparatus according to a first embodiment.

FIGS. 4A to 4K is a diagram to show examples of indicator available to present blood pressure value in embodiments.

FIG. 9 is a diagram to explain an example of a conventional report on the changes over time in blood vessel elasticity indexes.

DETAILED DESCRIPTION OF THE PREFERRED EMBODIMENTS

Preferred embodiments of the present invention will be specifically described below in accordance with the accompanying drawings.

First Embodiment (Configuration)

Figure 1:
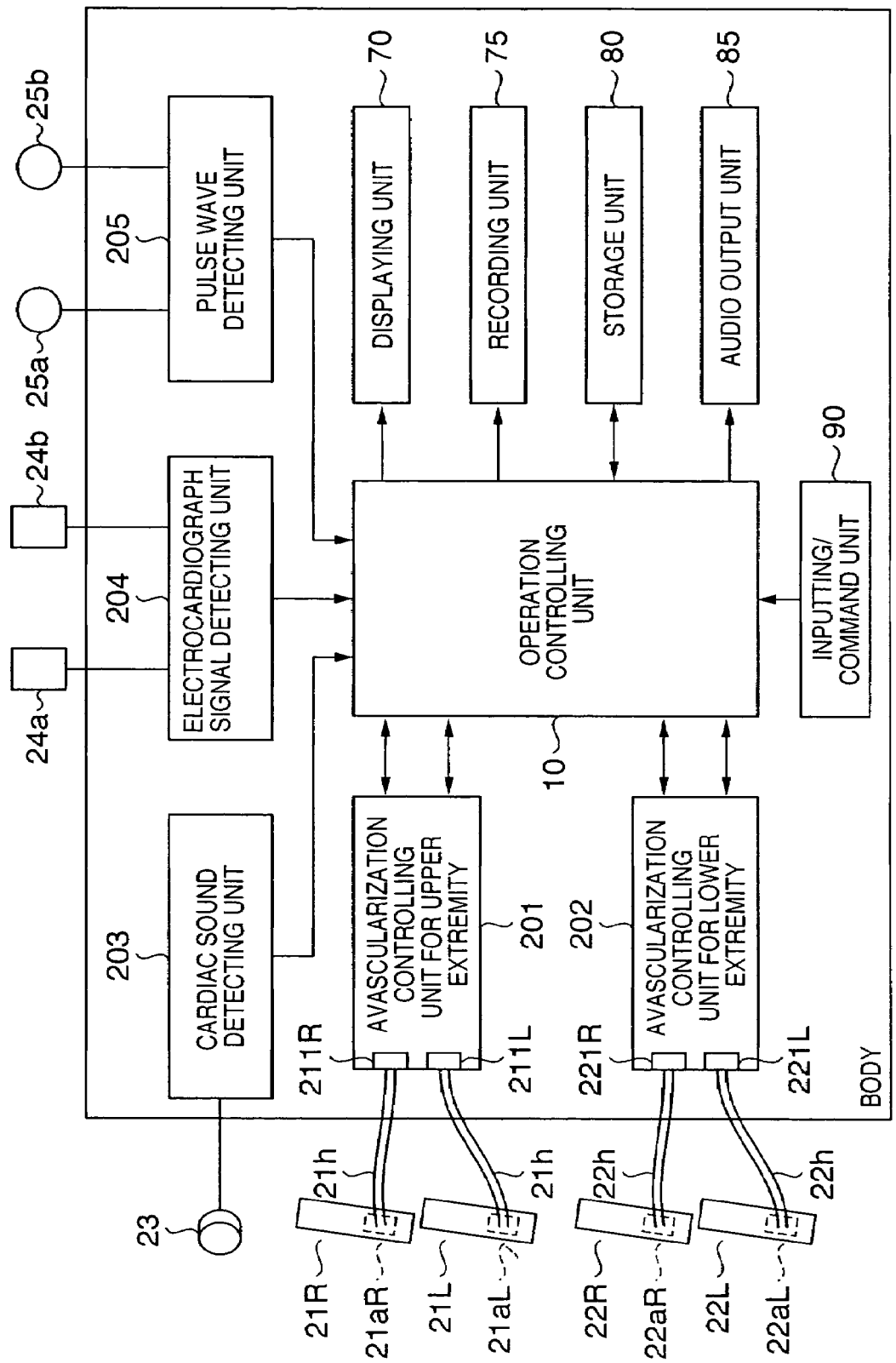
FIG. 1 is a block diagram to show a configuration of a bioinformation measuring apparatus as an example of a bioinformation output apparatus according to an embodiment of the present invention.

FIG. 1 is a block diagram to show a configuration of a bioinformation measuring apparatus as an example of a bioinformation outputting apparatus according to an embodiment of the present invention.

An operation controlling unit 10 controls the entire operation of a bioinformation measuring apparatus of this embodiment. The operation controlling unit 10 is, for example, a general purpose computer device comprising CPU, ROM, RAM (including nonvolatile RAM), and various interfaces (now shown), and performs and controls various operations which will be explained below by executing a controlling program stored in an built-in or external hard disk, a mass storage device such as optical disk or ROM with the CPU. Of course, the operations may be partly achieved by hardware, instead of all the operations being processed by software.

The operation controlling unit 10 measures, based on pulse wave information obtained by an avascularization controlling unit for upper extremity 201 and an avascularization controlling unit for lower extremity 202, systolic blood pressures Ps in brachium, ankle and toe. The operation controlling unit 10 determines, using the measurement results, an ABI (a ratio between a systolic blood pressure value in right or left ankle and a brachial (typical) blood pressure value) and a TBI (a ratio between a systolic blood pressure value in right or left toe and a brachial (typical) blood pressure value). The operation controlling unit 10 also determines diastolic blood pressures Pd and mean blood pressures Pm.

The operation controlling unit 10 also calculates a pulse wave propagation velocity between heart (aortic valve opening) and ankle or between heart and toe, by using pulse wave signals supplied from the avascularization controlling unit for upper extremity 201 and the avascularization controlling unit for lower extremity 202 (cardiac sound signals supplied from a cardiac sound detecting unit 203, electrocardiograph signals supplied from an electrocardiograph signal detecting unit 204, and carotid pulses, femoral arterial waves and popliteal arterial waves supplied from a pulse wave detecting unit 205, etc., may also be selectively used as needed) and a length of a blood vessel between the sites to be measured (a predetermined value corresponding to the length of blood vessel).

Then, the operation controlling unit 10 calculates bioinformation which presents a blood vessel elasticity (hereinafter, referred to as blood vessel elasticity index), based on any one of the formulae 1 to 5 shown in FIG. 2 for example. Note that either a left formula or right formula (the square root of the left formula) out of the formulae 1 to 5 shown in FIG. 2 may be selected for use.

The avascularization controlling unit for upper extremity 201 and the avascularization controlling unit for lower extremity 202 are controlled by the operation controlling unit 10 to control the pressurization/depressurization (avascularization) of rubber bladders (21aR, 21aL, 22aR, 22aL) of cuffs 21R, L and 22R, L connected two by two via hoses 21h and 22h, by using a pump or an exhaust valve (not shown). The avascularization controlling unit for upper extremity 201 and the avascularization controlling unit for lower extremity 202 also include a sensor to detect the pulse waves which propagate through the hoses 21h and 22h, such as pressure sensors (211R, L and 221R, L), for converting the pulse waves which propagate through rubber bladders and the hoses into electrical signals, and output the signals to the operation controlling unit 10. In FIG. 1, the avascularization controlling unit for upper extremity 201 and the avascularization controlling unit for lower extremity 202 are separately provided, but these units may be integrally provided as a single unit.

The cardiac sound detecting unit 203 supplies a cardiac sound signal of a subject, which are detected with a cardiac sound microphone 23, to the operation controlling unit 10. The cardiac sound signal is mainly used to determine a timing when the pulse waves start in the heart.

The electrocardiograph signals detecting unit 204 obtains electrocardiograph signals detected by electrocardiograph electrodes 24a and 24b to supply to the operation controlling unit 10. The electrocardiograph signals are obtained as needed when a more total diagnosis should be made.

The pulse wave detecting unit 205 supplies the pulse waves, specifically carotid pulses, femoral arterial waves or popliteal arterial waves, detected by the pulse wave sensors 25a and 25b to the operation controlling unit 10.

The operation controlling unit 10 is also connected to: a displaying unit 70 which is capable of displaying various operation guidance, measurement results and diagnosis indicators; a recording unit 75 which is capable of recording and outputting the measurement results and diagnosis indicators; a storage unit 80 consisting of, for example, a hard disk drive, a writable optical disk drive, a nonvolatile semiconductor memory to store the measurement results and diagnosis indicators; an audio outputting unit 85 which is capable of outputting an audio guidance or various reporting sounds; and an inputting/command unit 90 constituting of a keyboard, a mouse, a button, a touch panel and the like to enable inputs and commands by a user.

Other than those described above, a wire and/or wireless communication interface to communicate with other devices, or a storage device using a removable medium may be provided. The displaying unit 70 and the recording unit 75 may be configured to be separately connected to the external. That is, an external display device which has a larger display area and/or has more colors for displaying, or an external recording device which has a larger print area and/or has more colors for printing may be connected, other than the displaying unit 70 and the recording unit 75 which are provided in the device body. In this way, a compact body and various outputting are simultaneously achieved. In this case, a well-known display interface and a printer interface may be provided.

(Measurement Process: Preparation Before Measurement)

Now, procedure and operation for the measurement with a bioinformation outputting apparatus having the above described configuration will be explained. Here, the explanation is for the most accurate measurement. It assumed that an initialization process for device operations such as a time setting was completed in advance. For simplicity of explanation and understanding, a measurement by using one cuff for upper extremity and one cuff in lower extremity will be described below out of two sets of cuffs, but of course, a measurement with all the four cuffs is possible.

First, as a preparation step, cuffs, sensors and the like are attached to a subject. Specifically, the cuff for upper extremity 21R is attached to the right brachium of the subject, and the cuff for upper extremity 22R is attached to the ankle or toe of the subject. Practically the cuffs for ankle and toe have different configurations, but herein the both types of cuffs are explained as a cuff for lower extremity 22R. The cuffs 21 and 22 may be attached by means of a hook and loop fastener and the like. The electrocardiograph electrodes 24a and 24b are attached, for example, to right and left wrists. The attachment sites are applied with cream as usual for better detection. The attachment sites for the electrocardiograph electrodes may be changed depending on the type of lead to be obtained.

The cardiac sound microphone 23 is sticked to a predetermined position on the chest of the subject (sternal edge in the second intercostal space) with a tape or the like. Also, a pulse wave sensor 25a is sticked to carotid stroke site on the neck. If needed, a pulse wave sensor for femoral artery 25b is sticked on the groin.

Next, individual information of the subject such as age, sex, height, weight, and the like are input by using the inputting/command unit 90. Also, the lengths of blood vessel between the sternal edge in the second intercostal space and the respective sites where the cuff 21 and cuff 22 is attached are input by measuring each of the distances with a scale or the like (or by converting measured values). This is the end of the preparation before measurement.

(Measurement Process: Measurement of ABI)

After the measurement preparation is completed, and, for example, a command to start measurement is issued from the inputting/command unit 90, the operation controlling unit 10 first starts a blood pressure measurement process to measure an ABI. The operation controlling unit 10 issues a command to the avascularization controlling unit for upper extremity 201 first, though the priority of the order may be optionally set, to start pressurization on the right brachial cuff 21R.

The avascularization controlling unit for upper extremity 201 feeds air to the cuff 21R and inflates the rubber bladder 21aR. The pulse wave propagates as a pressure wave from the rubber bladder 21aR via the hose 21h to the pressure sensor 211R, where the pulse wave is detected. The pulse wave is converted to an electrical signal (generally, the pressure sensor itself converts the pressure into an electrical signal and outputs it), and is output as a pulse wave signal obtained from the cuff 21R to the operation controlling unit 10.

The operation controlling unit 10 controls the avascularization controlling unit for upper extremity 201 to continue to feed air to the rubber bladder 21aR until a pulse wave is not detected by the pressure sensor 211R, that is until an avascularization is induced, and at the point when no more pulse wave is detected, the pressurization is stopped. The cuff pressure at this point can be detected by the pressure sensor 211R. Then the operation controlling unit 10 issues a command to the avascularization controlling unit for upper extremity 201 to gradually reduce the cuff pressure.

The avascularization controlling unit for upper extremity 201 depressurizes the cuff at a constant rate by adjusting the exhaust valve (now shown) and exhausting air from the rubber bladder 21aR. During the depressurization, a systolic blood pressure Ps, a mean blood pressure Pm, and a diastolic blood pressure Pd are determined from the cuff pressures at the point when the amplitude of a pulse wave rapidly increases after the detection of pulse wave is resumed, at the point when the amplitude of a pulse wave is the largest, and at the point when the amplitude of a pulse wave rapidly decreases, respectively. These cuff pressures can be calculated from the pressure value at the point when the depressurization started, the depressurization rate and the period of time of the depressurization. This type of blood pressure measurement is known as an oscillometric method (plethysmography). After the diastolic blood pressure is determined, the cuff is depressurized rapidly. The above described blood pressure measuring process is similarly performed on the other cuff(s) to complete the blood pressure measurement in the upper extremity and the lower extremity.

Using the determined blood pressures, the operation controlling unit 10 calculates an ABI as follows, for example:

ABI=a systolic blood pressure value in right ankle/a blood pressure value in right brachium The measured systolic blood pressure value, the mean blood pressure value and the diastolic blood pressure value as well as the calculated ABI are recorded in the storage unit 80.

(Measurement Process: Measurement of TBI)

The cuff for measurement in lower extremity 22R is attached to toe (for example, great toe of right foot) to measure and calculate a TBI as in ABI. The calculated TBI is recorded in the storage unit 80.

(Measurement Process: Measurement of PWV)

Next, a PWV is measured. In case that carotid pulses are detected with a pulse wave sensor 25a, the operation controlling unit 10 obtains the pulse waves via the pulse wave detecting unit 205, while detecting the generation of cardiac sound (e.g. the second heart sound) corresponding to a rising point of pulse wave from the cardiac sound signals obtained via the cardiac sound detecting unit 203. The pulse waves and cardiac sound signals are recorded in the storage unit 80 after appropriate processes such as A/D conversion are applied. Then a PWV is determined from the following formula:

$$PWV = AF/(t+tc)$$

where,

AF: a length of the blood vessel from the sternal edge in the second intercostal space to the cuff 22R attachment site (ankle or toe), t: a time difference between the rising point in a carotid pulse (or a brachial pulse) and the rising point in an ankle (or toe) pulse wave, and tc: a time difference between the rising point in second sound of cardiac sound and the notch point in a carotid pulse (or a brachial pulse wave).

In case that the pulse wave sensor 25a is not used, a PWV is measured by using the pulse wave rising point measured with the cuff 21R which is attached to a brachium.

After the measurement of the PWV is completed, the operation controlling unit 10 controls the avascularization controlling unit for upper extremity 201 and avascularization controlling unit for lower extremity 202 to evacuate the cuff, records the measurement results in the storage unit 80, and ends the process for measurement.

As described above, this embodiment has been explained with a case in which the measurement of blood pressure and pulse wave is performed only on right brachium, right ankle, and right toe, but the measurement of blood pressure and pulse wave may be similarly performed on left brachium, left ankle, and left toe. Also as for a PWV, two values on heart—ankle and on heart—toe may be calculated, or four values may be calculated for the right and left respectively.

(Calculation of Blood Vessel Elasticity Index)

Next, the operation controlling unit 10 calculates a blood vessel elasticity index. As a blood vessel elasticity index, a value obtained from Formulae 1 to 5 in FIG. 2 may be used. In Formulae 1 to 5, k is a constant. A formula should be chosen in advance to use for calculation of a blood vessel elasticity index. Of course, two or more formulae may be chosen to use for calculation of a blood vessel elasticity index.

Figure 8:
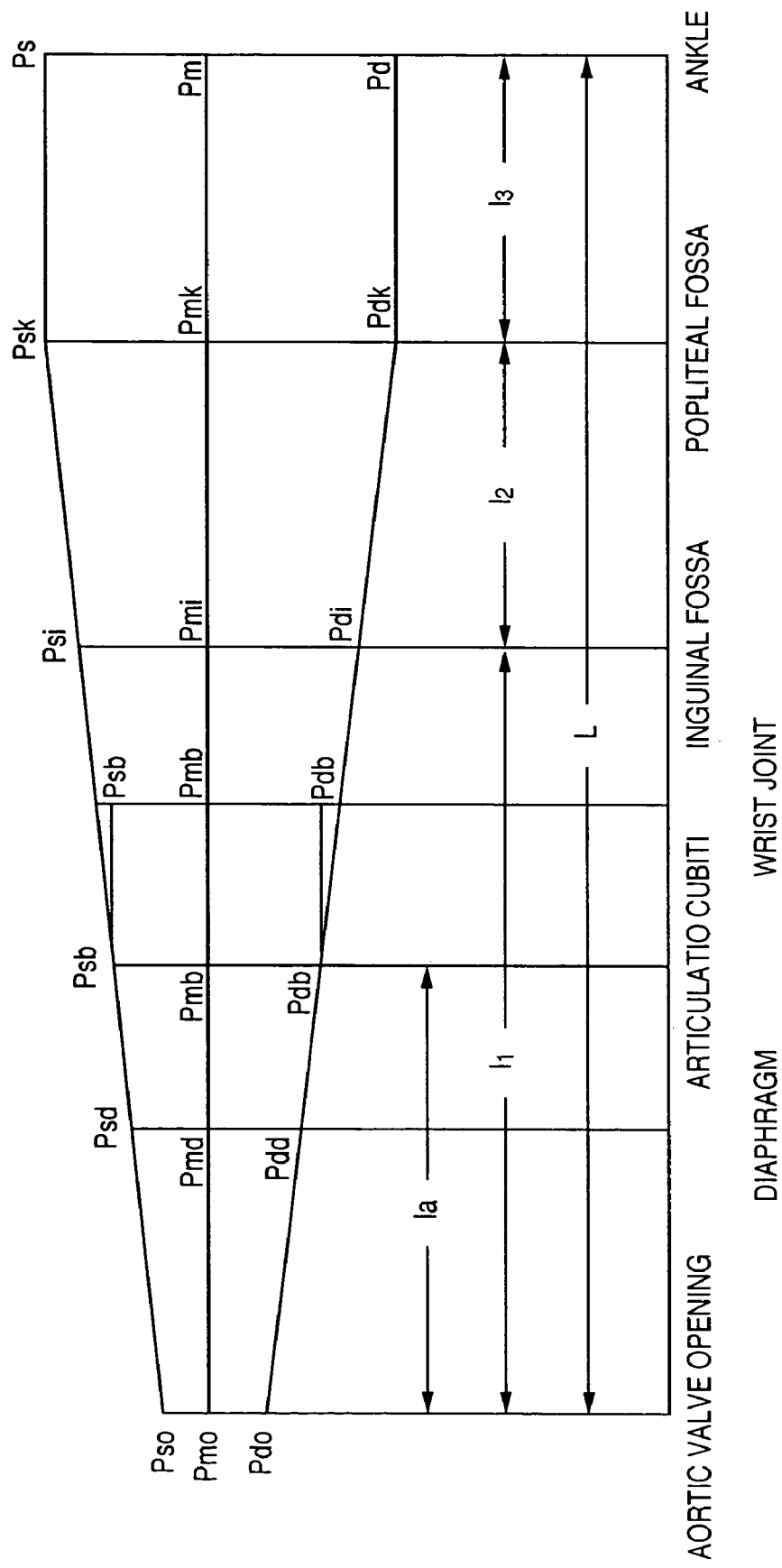
FIG. 8 is a diagram to show a systematic body blood pressure distribution characteristic, which is used in the estimation of a blood pressure value that is used when a bioinformation output apparatus according to an embodiment calculates a blood vessel elasticity index.

Ideally, the blood pressure values Ps, Pm and Pd used in Formulae 1 to 5 are the values measured at the center of cites where the PWV was measured. However, for example, the values measured in brachium may be used instead. The values at the center point may be estimated, for example, by measuring blood pressures at the sites where the pulse waves were measured to calculate a PWV and applying the blood pressures to a precalculated conversion formula. Specifically, a blood pressure value in a site between the measurement cites can be estimated from the characteristics of a systematic body blood pressure distribution such as those shown in FIG. 8 and the values measured at two points of sites shown in the characteristic figure.

The above estimation uses a fact derived form the characteristics of a systematic body blood pressure distribution, i.e., both a Ps and a Pd linearly increase or decrease from aortic valve opening to popliteal fossa and a Pm is almost constant through the cites. Specifically, for example, when a systolic blood pressure Psi in inguen is estimated from a systolic blood pressure Ps in ankle and a systolic blood pressure Psb in brachium, a relational formula:

(Ps−Psb):(distance between ankle−brachium)=(Psi−Psb):(distance between inguen−brachium)

may be used to estimate a Psi. Similarly, a Pdi may be estimated from a Pd and a Pdb. In order to calculate a blood vessel elasticity index, either PWV measured between heart—ankle or heart—toe may be used.

The various measured bioinformation including blood pressures (systolic blood pressures Ps, diastolic blood pressures Pd, and mean blood pressures Pm), the calculated values such as an ABI, a TBI, a PWV and a blood vessel elasticity index, and other any information are stored in the storage unit 80, associated with the individual information of the measured subject and the date and time when the measurement is performed. For example, a folder or a directory is created for each subject and whenever a measurement is performed, a new folder or directory for the measurement is further created in the folder or directory for the subject to store the bioinformation, calculated parameters, and obtained wave form information and the like.

In this embodiment, since the bioinformation output apparatus has functions to obtain various bioinformation, a measurement process for ABI, TBI and PWV, and a calculation process of blood vessel elasticity index were explained as the operations of the apparatus. However, all the function the bioinformation output apparatus according to the present invention must have is that to obtain blood pressure values and blood pressure elasticity indexes of a common patient with its measurement date and time information, and the functions to measure bioinformation are not essential. In other words, any apparatus which is able to generate and output a report, which will be explained below, with respect to blood pressure values and blood pressure elasticity indexes of a common patient and has no configuration for other operations may be used.

(Report Outputting Process)

Figure 5:
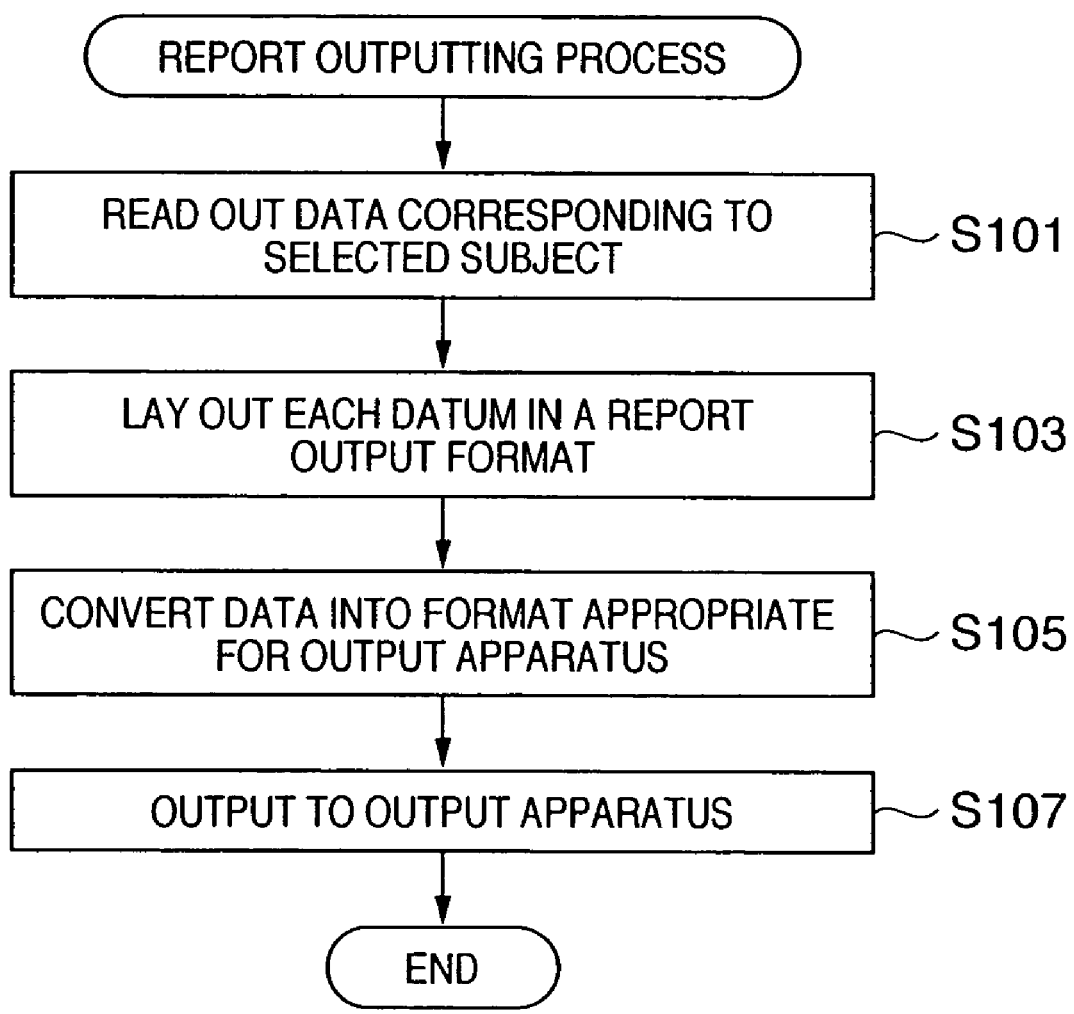
FIG. 5 is a flowchart to explain a process to output a report on changes over time with a bioinformation output apparatus according to an embodiment of the present invention.

Now, a report outputting process with the above described bioinformation output apparatus will be explained below with reference to the flowchart of FIG. 5. In this embodiment, it is assumed that a process to output a report in a format which will be explained below is achieved by executing a report outputting program with the operation controlling unit 10 and the report is output to the displaying unit 70 or the recording unit 75. However, this report outputting process may be achieved by executing a similar program in apparatuses other than the bioinformation measuring apparatus, such as a bioinformation analyzing apparatus, or more generally, a computer device commercially available as a personal computer. Also, a report may be output, as described above, to an external display device or an external output apparatus.

The report outputting process may be automatically performed after measurement by obtaining the past measurement results of the subject, or may be performed, for example, by displaying a list of the subjects whose information have been measured and recorded in the storage unit 80 on the displaying unit 70, and outputting the measurement results of the subjects selected from the list through the inputting/command unit 90. In this embodiment, the measurement results of the subjects selected from a list of subjects to whom the measurements were performed before are output.

First, the operation controlling unit 10 reads information required to generate a repot such as the individual information and measurement results (blood pressure values, blood pressure elasticity index or the like) on the selected subjects out of the storage unit 80 (step S101). Then the operation controlling unit 10 lays out the read out information in an output format which will be explained below (step S103).

After the laying out, the operation controlling unit 10 converts the formatted information to data having a format that it can be output by the output apparatuses such as the recording unit 75 (step S105). The format conversion includes a change in resolution depending on the output apparatus (e.g. 72 or 96 dpi for displaying, and 400 to 600 dpi for printing), a change in color depth (e.g. change into monochrome, increase or decrease of color numbers), a scaling down/up, and a generating bitmap data. After the format is changed to be suitable for the output apparatuses, the changed data is output to the output apparatus as a report data (step S107), where it is displayed or printed out.

If the measurement data is in a state to be obtainable by the bioinformation output apparatus by means of for example a network or a removable storage medium such as a memory card or optical disk, the data can be output in a similar process even when a bioinformation output apparatus without a function to measure bioinformation outputs a report. That is, the bioinformation output apparatus first obtains a list of information on the measurement data (e.g. a list of subject names) and displays it on a display screen. After a subject is selected by means of an input device such as keyboard and mouse, a process is performed as in the above described steps S101 to S105 to output the information to the preset output apparatuses such as a display or a printer (step S107). This allows a similar report to be displayed or printed out.

(Report Format)

FIG. 3 is a diagram to explain a format of a report on changes over time which is output with a bioinformation output apparatus according to this embodiment. The report on a change over time presents the changes over time in blood vessel elasticity indexes (on at least one of right side body and left side body) and in measured values of at least one or more kinds of bioinformation related to vascular diseases. In this embodiment, blood pressure values are presented as bioinformation related to vascular diseases. And as the blood pressure values, a maximum (systolic) blood pressure value, a mean blood pressure value, and a minimum (diastolic) blood pressure value are presented.

The report includes a two dimensional graph area with orthogonal axes: one vertical axis has scales for blood vessel elasticity indexes, and the other vertical axis has scales for blood pressures; a horizontal axis represents time, and has scales for dates on which each value was measured. As described above, blood pressure values are also measured to calculate blood vessel elasticity indexes, thereby there are corresponding measured results between the blood vessel elasticity indexes and the blood pressure values, which are plotted in association with each other for each measurement date.

As for the blood vessel elasticity indexes, at least one of the values on right side body and the values on left side body, preferably both of them are presented. The blood vessel elasticity indexes are plotted in time series by placing indicators (•) in the coordinates defined by the measurement time and the value in the graph area, and for easy identification of the changes over time, the adjacent indicators in the same sequence are connected by a line. Close to each indicator of a measured value, the specific measured value is presented. Further, in this embodiment, when both the measured values on right side body and the measured values on left side body are presented, the sequence of the measured values on right side body and the sequence of the measured values on left side body are presented with different expressions (in this embodiment, different tones) for easy visual discrimination. Of course, other expressions may be used including different colors, and different shapes of the indicators. However, it is desirable to use an expression which does not reduce the visibility of the straight lines connecting the indicators.

In this embodiment, a systolic blood pressure value, a mean blood pressure value, and a diastolic blood pressure value, which are measured together with a blood vessel elasticity index, are presented in association with the corresponding blood vessel elasticity index in the graph area in time series. Advantageously, each of the blood pressures is presented as an indicator in a form which is easy to discriminate from the corresponding blood vessel elasticity index and is not complicating, and is located close to the indicator of the corresponding blood vessel elasticity index and on a coordinate (along the vertical axis) which corresponds to the blood pressure value.

In FIG. 4, an example of an indicator to present a blood pressure value is shown. FIGS. 4A and 4B show the simplest form, and a systolic blood pressure value, a mean blood pressure value, and a diastolic blood pressure value are plotted as the same marks arranged in a generally vertical direction. Any shape of mark may be selected unless it reduces the visibility of the indicator, and the horizontal lines and circles used in FIGS. 4A to 4K are only for illustration.

FIGS. 4C and 4D show the forms with straight lines added to those in FIGS. 4A and 4B. The straight lines are connecting the centers of each mark, and the indicators are divided into symmetry shapes. While, FIGS. 4E to 4G show indicators which are divided into asymmetry shapes so that the indicators have directions. FIGS. 4E and 4F show the marks which are connected by a straight line not at the centers but at the ends of the marks so that the marks have directions, and FIG. 4G shows a mark of a shape which has a direction by itself. This provides a visual understanding of on which side of body the blood pressure values of the indicators were measured.

In FIG. 3, the indicators of ∃ shape shown in FIG. 4E are used to indicate that the blood pressure values were measured on the right side body. The indicators to indicate the blood pressure values measured on the other side body have mirror reversed shapes of those of FIGS. 4E to 4G. Thus, the opposite indicator corresponding to that of FIG. 4E has an E shape. When an asymmetry indicator or a directional indicator is used, the relations between the indicator and the left or right side body may be optionally defined. For example, in FIG. 3 an indicator of ∃ shape may be used to illustrate a blood pressure value on left side body, and an indicator of E shape may be used to illustrate a blood pressure value on right side body. However, when the report has another information on the left and right sides, the indicators are preferably related to the corresponding values in a consistent way with the expressions for the other information, which will be explained in detail below.

FIGS. 4H to 4K show the indicators with different a shape, size, and an inside expression of a mark depending on the kind of a blood pressure value. In this embodiment, the mark for a mean blood pressure value is shown as a different shape from those for systolic and diastolic blood pressure values, but every kind of blood pressure value may have a different shape, or one kind of blood pressure values other than the mean blood pressure values may have a different shape from the other two. FIG. 4H shows the indicators of a common shape of a horizontal line, and the mark for the mean blood pressure value is shorter than the others, FIG. 4I shows the indicators of a common contour, and the inside expressions (in this embodiment, color or fill pattern) are different, and FIGS. 4J and 4K show the indicators of different shapes.

The shape of a mark can be changed, both in the case of symmetry indicators such as those of FIGS. 4I, 4J and in the case of asymmetry indicators such as those of FIGS. 4H, 4K.

Further, when a blood pressure value is out of a predetermined normal range, the value may have a mark with a different shape, size or inside expression from those in normal ranges. This provides an easy understanding if the blood pressure value is an abnormal value or not without plotting specific measured values. So this allows users to understand if the blood pressure value is an abnormal value or not while preventing the possible reduced visibility due to a plotting of measured values.

The indicator for a blood pressure value is not necessarily placed on the same coordinate along the horizontal axis with the indicator for a blood vessel elasticity index as far as the indicator is positioned so that the relations between the corresponding blood vessel elasticity index can be intuitively understood, and may be horizontally offset as shown in FIG. 3. When an indicator is horizontally offset, the offset direction may have the same function as in the directionality of an indicator. In FIG. 3, in presenting an indicator for a blood pressure value, the indicator for a blood pressure value is offset to the right of the corresponding indicator of a blood vessel elasticity index, thereby not only the directionality of the indicator itself but also the location of the indicator suggest that the blood pressure values were measured on the right side body.

As explained above, according to this embodiment, the values of blood vessel elasticity indexes which were measured over time are presented in time series, and the other bioinformation values related to vascular disease which were measured simultaneously with the indexes are also presented. This makes it possible to compare and examine the blood vessel elasticity indexes and their changes over time, and the blood pressure values and their changes over time, and is useful to determine, for example, if hypotensive drug should be administered or not.

As described above, because a blood vessel elasticity index less depends on a blood pressure than a pulse wave propagation velocity does, it is sometimes difficult to understand a change in blood pressure values only from the blood vessel elasticity indexes. So it has a unique effect in presenting both blood vessel elasticity indexes and blood pressure values to enable a check of the presence or absence of a change in blood pressures.

Further, because a blood pressure value is presented by a characteristic indicator, a practical value of a blood pressure value or any change in blood pressure values can be easily understood without degrading the readability of blood vessel elasticity indexes.

Second Embodiment

Now, a bioinformation output apparatus according to a second embodiment of the present invention will be explained. Because the bioinformation output apparatus of this embodiment is the same as the apparatus of the first embodiment except for a report format to be output, only the report format, which is a characteristic feature of this embodiment, will be explained.

Figure 6:
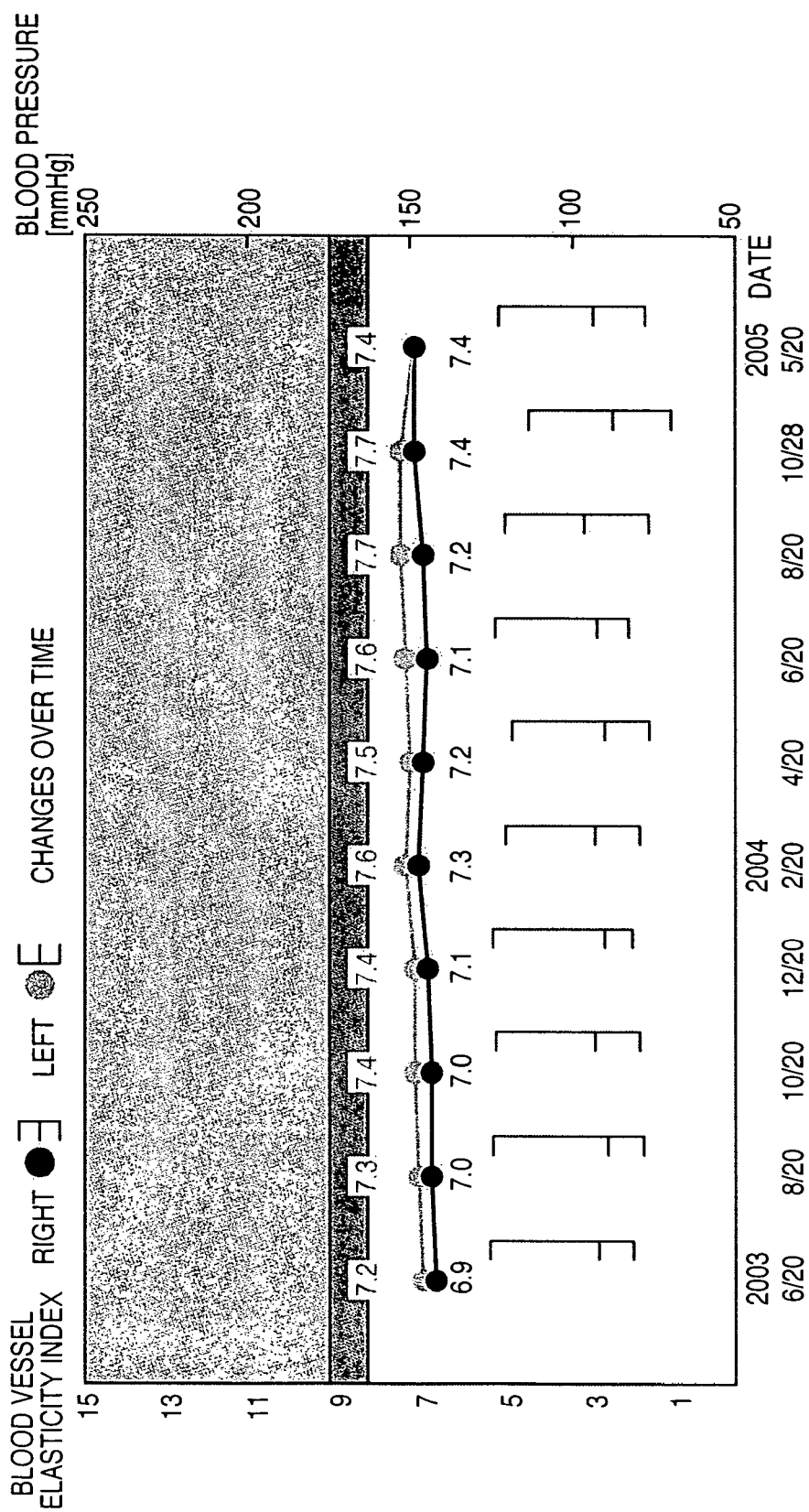
FIG. 6 is a diagram to explain a format of a report on changes over time, which is output with a bioinformation output apparatus according to a second embodiment.

FIG. 6 is a diagram to explain a format of a report on changes over time, which is output with a bioinformation output apparatus according to this second embodiment. A format of this embodiment is basically the same with that of the first embodiment, and is characterized in that the areas are divided according to a range of numeric values of blood vessel elasticity indexes.

In this embodiment, the divisions are expressed by means of variations of different fill patterns, but this is only an example of a way of division, and any method may be used if the divisions of the area can be recognized, including a method to change the tone of colors or the shading of meshes, as well as to surround the area by lines.

The following is the baseline for dividing an area and the possible vascular state when the measured value is included in each area:
(1) blood vessel elasticity index$\geqq 10.0$: severe arteriosclerosis
(2) $9.0\leqq$blood vessel elasticity index$<10$: heavy arteriosclerosis
(3) $8.0\leqq$blood vessel elasticity index$<9.0$: moderate arteriosclerosis
(4) blood vessel elasticity index$<8$: normal In FIG. 6, both areas corresponding to (1) and (2) are expressed as one area because both (1) and (2) suggest severe states. However, these areas may be expressed individually.

In this way, according to this embodiment, a report is output in a format in which an area is divided based on the values of blood vessel elasticity indexes, so that the way the values of blood vessel elasticity indexes change can be understood more easily, in addition to the effect of the first embodiment.

Other Embodiment

Figure 7:
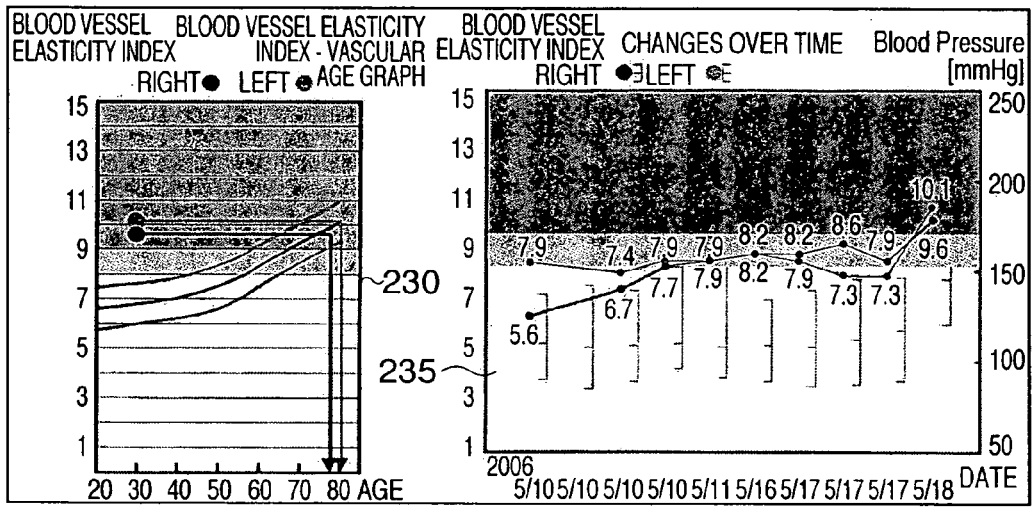
FIG. 7 is a diagram to show an example a comprehensive report which includes a report on changes over time according to an embodiment.

FIG. 7 is a diagram to show an example a comprehensive report on the common subject as in the first embodiment, which includes the report on changes over time in the format according to the first embodiment as a part. This comprehensive report includes, from the top to the bottom, a section for bibliographic information 210 to present measurement date and individual information on subject, a section for first measured results 220 to present the current measured values of blood vessel elasticity indexes and ABI and a comment corresponding to the measured values, a vascular age graph 230 to illustrate a vascular age estimated from the current blood vessel elasticity indexes, a graph of change over time 235 in the format described in the above embodiments, a blood pressure presenting section 240 to present the current results of the measured blood pressures, and a section for observation 250 to present a state of vascular disease estimated from the measured results of the blood vessel elasticity indexes and ABI.

In this embodiment, in the blood pressure presenting section, a schematic illustration of an entire human body is used to present the blood pressure measured values (systolic/diastolic, (mean)) and pulse pressures in right and left upper and lower extremities which are positioned to be in the mirror image relation with the report observer. That is, on the left side of the report is illustrated the right side body. Thus, similarly in the graph of changes over time 235, the indexes of ⊒ shape correspond to the blood pressure values in the right side body.

As described above, the report outputting process in each embodiment may be performed, for example, with a computer device which reads the blood pressure values and the blood vessel elasticity index measured in advance out of a storage device which stores the values, and outputs a report of an above described format. Therefore, needless to say, any program which makes the computer device execute the report outputting process in each above described embodiment, or any computer readable recording medium which stores the program are also included in the present invention.

As many apparently widely different embodiments of the present invention can be made without departing from the spirit and scope thereof, it is to be understood that the invention is not limited to the specific embodiments thereof except as defined in the claims.

What is claimed is:

1. A method of reporting changes over time in blood vessel elasticity indexes to present the changes over time of measured results of blood vessel elasticity indexes with respect to a common subject, comprising:
   providing a graph area with a horizontal axis representing time and a vertical axis representing values of blood vessel elasticity indexes;
   plotting in time series each of the blood vessel elasticity indexes by positioning a first indicator at a coordinate defined by a measured time and a value in the graph area;
   plotting in time series a measured value of bioinformation relative to vascular disease other than the blood vessel elasticity index and measured together with the blood vessel elasticity index in the graph area in association with the corresponding blood vessel elasticity index;
   representing the measured value of bioinformation by another vertical axis of the graph area; and
   plotting the measured value of bioinformation with a second indicator located close to the first indicator of the corresponding blood vessel elasticity index and on a coordinate corresponding to the measured value of bioinformation.

2. The method according to claim 1, wherein the measured value of bioinformation is a blood pressure value.

3. The method according to claim 2, wherein the second indicator comprises three marks which are arranged in a vertical direction to present a systolic blood pressure value, a mean blood pressure value, and a diastolic blood pressure value.

4. The method according to claim 3, wherein the second indicator further comprises a straight line connecting the three marks.

5. The method according to claim 3, wherein at least one of the three marks has a different shape or size from the others.

6. The method according to claim 3, wherein the shape or size of the marks changes depending on the relationship between the normal ranges predetermined for each of the systolic blood pressure value, the mean blood pressure value, and the diastolic blood pressure value and the measured values illustrated by the marks.

7. The method according to claim 1, wherein the second indicator has an asymmetry shape, the directionality of which indicates whether the measured value of bioinformation is for right or left side body.

8. The method according to claim 1, wherein the second indicator which is offset to the right or left of the corresponding blood vessel elasticity index indicates whether the measured value of bioinformation is for right or left side body.

9. The method according to claim 1, wherein the graph area is divided into a plurality of areas depending on the values of the blood vessel elasticity index.

10. A bioinformation output apparatus, comprising:
    obtaining means for obtaining from a storage device, measured values of at least a blood vessel elasticity index and other bioinformation related to one or more vascular diseases which are measured in a common subject;
    report generating means for generating a report on changes over time in the blood vessel elasticity index; and
    outputting means for outputting the generated report on the changes over time in blood vessel elasticity indexes,
    wherein the report generating means generates a report on changes over time in blood vessel elasticity indexes by providing a graph area with a horizontal axis representing time and a vertical axis representing values of blood vessel elasticity indexes, plotting in time series each of the blood vessel elasticity indexes by positioning a first indicator at a coordinate defined by a measured time and a value in the graph are, plotting in time series a measured value of bioinformation relative to vascular disease other than the blood vessel elasticity index and measured together with the blood vessel elasticity index in the graph area in association with the corresponding blood vessel elasticity index, representing the measured value of bioinformation by another vertical axis of the graph area, and plotting the measured value of bioinformation with a second indicator located close to the first indicator of the corresponding blood vessel elasticity index and on a coordinate corresponding to the measured value of bioinformation.

* * * * *